United States Patent
Portmann

(10) Patent No.: US 10,359,384 B2
(45) Date of Patent: Jul. 23, 2019

(54) FLEXIBLE SENSOR CIRCUIT ARRANGEMENT

(71) Applicant: Sentek Pty Ltd., South Australia (AU)

(72) Inventor: Michael Portmann, South Australia (AU)

(73) Assignee: SENTEK PTY LTD., Stepney, South Australia (AU)

(*) Notice: Subject to any disclaimer, the term of this patent is extended or adjusted under 35 U.S.C. 154(b) by 339 days.

(21) Appl. No.: 15/303,094

(22) PCT Filed: Apr. 10, 2015

(86) PCT No.: PCT/AU2015/000205
§ 371 (c)(1),
(2) Date: Oct. 10, 2016

(87) PCT Pub. No.: WO2015/154129
PCT Pub. Date: Oct. 15, 2015

(65) Prior Publication Data
US 2017/0030852 A1    Feb. 2, 2017

(30) Foreign Application Priority Data

Apr. 10, 2014  (AU) ................. 2014901327

(51) Int. Cl.
*G01N 33/24*  (2006.01)
*G01N 27/22*  (2006.01)
*G01R 27/26*  (2006.01)

(52) U.S. Cl.
CPC .......... *G01N 27/223* (2013.01); *G01N 33/246* (2013.01); *G01R 27/26* (2013.01); *G01R 27/2605* (2013.01)

(58) Field of Classification Search
CPC ............... G01N 27/223; G01N 33/246; G01R 27/2605; G01R 27/26
See application file for complete search history.

(56) References Cited

U.S. PATENT DOCUMENTS 2,793,527 A    5/1957   Turner, Jr. et al.
4,909,070 A    3/1990   Smith
(Continued)

FOREIGN PATENT DOCUMENTS

AU         760525 B2      5/2003
WO     2004/109238 A1    12/2004
(Continued)

OTHER PUBLICATIONS

Corrected International Search Report and Written Opinion, including original Written Opinion, for International Application No. PCT/AU2015/000205, dated Jun. 29, 2015, 19 pages.

*Primary Examiner* — Amy He
(74) *Attorney, Agent, or Firm* — Westman, Champlin & Koehler, P.A.

(57) ABSTRACT

The field is sensors used in the ground and in particular the provision of a sensor array element for a sensor array useable in housing that has a tapered internal and external shape. The lack of air spaces and gaps, in particular, between the outer surface of the hollow elongate sensor housing and the surrounding ground is substantially avoided when using a tapered housing. A sensor array element is disclosed including a carrier sheet of flexible material formable into a shape which substantially conforms with the shape of the inner wall of said elongate housing. The carrier sheet has electrically conductive regions wherein at least one pair of electrically conductive regions are shaped and located near enough each other to form a capacitive element. The carrier sheet has at least two pairs of electrically conductive regions forming a pair of capacitive elements, and adjacent pairs of capacitive elements have a different diameter. When the carrier sheet is shaped to substantially conform to the inner wall of the elongate housing and the capacitive element connected to a tuned circuit, the capacitive element and tuned circuit are usable to sense at least the moisture content (Continued)

of the environment surrounding the location of the capacitive element located within the elongate housing. The disclosure is also of a sensor and a sensor array incorporating a sensor array element.

17 Claims, 3 Drawing Sheets

(56) References Cited

U.S. PATENT DOCUMENTS

| | | | |
|---|---|---|---|
| 4,929,885 A | | 5/1990 | Dishman |
| 5,260,666 A | * | 11/1993 | Dishman .............. G01N 27/223 324/664 |
| 5,418,466 A | | 5/1995 | Watson et al. |
| 7,042,234 B2 | | 5/2006 | Buss |
| 7,240,743 B2 | | 7/2007 | Buss et al. |

FOREIGN PATENT DOCUMENTS

| | | |
|---|---|---|
| WO | 2008/052274 A1 | 5/2008 |
| WO | 2014/165910 A1 | 10/2014 |

* cited by examiner

FLEXIBLE SENSOR CIRCUIT ARRANGEMENT

CROSS-REFERENCE TO RELATED APPLICATIONS

This Application is a Section 371 National Stage Application of International Application No. PCT/AU2015/000205, filed 10 Apr. 2015 and published as WO 2015/154129 A1 on 15 Oct. 2015, in English, the contents of which are hereby incorporated by reference in their entirety.

The applicant is the applicant for many soil sensors as disclosed in U.S. Pat. No. 5,418,466; AU760525; AU20030331464; U.S. Pat. No. 7,042,234; 7,240,743 and WO20141165910. The information disclosed therein is incorporated by reference in its entirety into this specification. Yet further this application claims priority from AU2014901327 and the information disclosed therein is incorporated in its entirety by reference into this specification.

TECHNICAL FIELD

The field is sensors used in the ground and in particular the provision of a sensor array element for a sensor array useable in housing for use in the ground.

BACKGROUND

The field of elongate soil sensors includes many types of soil sensors but the shape of the housing that is inserted into the ground will largely be the same. The soil sensors are enclosed in housings, some examples of housings are disclosed in the abovementioned patents but in the main the housings are elongate to permit multiple sensors to be located along the internal length of the elongate housing, at various depths in the soil or material to be sensed. Of particular note is that the housings are all cylindrical and have a constant diameter along the full inserted length. The outer shape of the hollow elongate sensor housing is largely dictated by the shape of the active sensor element which is an element in a tuned circuit which is also part of a more complex moisture/complex dielectric constant sensor, which can if used appropriately, and as is described in detail in U.S. Pat. No. 5,418,466, provide salinity measurement or trend indications of the moisture of the soil within which the housing is inserted at the various depths of the sensor elements part of the sensor circuit.

In many soil sensors capacitive active elements are used as part of a tuned circuit and generally a capacitive sensor element is comprised of two metal plates physically separated at a fixed distance but located and arranged so that the electromagnetic field they generate and the effects of the field of influence of that generated field is maximally projected into and received from the surrounding soil, the characteristics of which are then measureable by way of analysis of the signal associated with the tuned circuit. In the soil moisture sensors disclosed in the referenced patent specifications, the plates are formed by metallic rings, typically having a height much greater than their thickness and a diameter that will determine or be determined by the frequency of operation of the tuned circuit. The sensor rings are in the main positioned so that the circular outer face of each ring of the pair of rings is close to the inner surface of the generally cylindrical housing, which in effect is close to the surrounding soil which is to be sensed by those sensors when in operation. Multiple pairs of rings are typically spaced 10 cm apart along the internal length of the housing to provide measurements of the soil characteristics at different depths in the ground.

The referenced sensor arrays are housed in elongate cylindrically shaped housings and the reasons for carefully creating a cylindrical opening in the ground, include the following:

a. To ensure that the ground in the immediate vicinity of the hollow elongate sensor housing and hence the sensors therein remains as undisturbed as possible.

b. That the physical fitment between the hollow elongate sensor housing and the surrounding ground is such that there is no gap or gaps between the surrounding soil and the outer surface of the elongate sensor housing along substantially its full length. Gaps, if they existed, would create the potential for the creation of preferential water seepage channels from the surface of the soil and in the immediate vicinity of the sensor, which will skew or make un-useable the readings of soil moisture and other characteristics of the surrounding soil detected by the sensor/s within the hollow elongate sensor housing. Further, there can be shadowing if the housing extends above the ground level that can also affect the moisture distribution in the immediate vicinity of the sensor.

Some of these characteristics do not become an issue if the gap or gaps do not exist but to achieve that outcome using the prior arrangements there is a need to ensure that the inner wall of the opening created by the auger is relatively smooth and of constant inner diameter along its full depth. This has been the intention of the techniques described in at least one of the referenced documents, in one example, by slightly under-sizing the opening created by the auger relative to the constant outer diameter of the inserted hollow elongate sensor housing, and cutting or slicing away a portion of the inner wall of the prepared opening with the inserted end of the hollow elongate sensor housing adapted to do that slicing as it is inserted into the prepared opening.

It will be noted in the referenced documents that the elimination of a gap or gaps between the hollow elongate sensor housing and surrounding soil is identified as a requirement for the proper operation of the in-situ soil sensor. However, the installation process described in those patents where constant diameter cylindrical hollow elongate sensor housings are used does not ensure that outcome every time. One problem encountered includes, that any wobbling of the auger by the operator during the creation of the opening can create larger excursions from the sheared volume created when the hollow elongate sensor housing with a cutting arrangement is inserted, such that gaps are left at one or more locations along the length of the inserted hollow elongate sensor housing. The gap, if air filled is substantial enough or if the gap is occupied by water, affects the sensor measurements in the gap regions and they will not be indicative of the soil characteristics in the field of influence of the sensor near or at those gap regions. Yet further, the type of soil can make a huge difference to how easy or hard it is to create a prepared opening because of the hardness, composition or even the current soil moisture content. It being known that if the soil is primarily clay then there will be considerable work in creating the prepared opening and sometimes as much work again inserting the hollow elongate sensor housing.

BRIEF DESCRIPTION OF ASPECTS OF VARIOUS EMBODIMENTS

None of the soil sensor housings disclosed in the referenced documents or known to the inventor have a housing including an elongate hollow sensor housing with a first end (referred to herein as the head end), a second end (referred to herein as an inserted end), and an outer surface being continuously tapered from the head end to the inserted end.

A reason to use a tapered outer shape for the hollow elongate sensor housing in a tapered opening is the realisation that the elimination of a gap between the outer surface of the hollow elongate sensor housing and the wall of the prepared opening is assured because the downward motion of the sensor into a complimentarily shaped opening ensures that the outer surface of the hollow elongate sensor housing will apply an even pressure over the total outer area of the full inserted length of the hollow elongate sensor housing against the soil surface forming the opening. The greater the downward force on the hollow elongate sensor housing the greater the pressure and the greater likelihood there will be no gaps between the outer area of the hollow elongate sensor housing and the soil surface forming the opening.

Thus is there a reason because of the development of such a housing by the owner common to this patent application and the patent application which covers such a housing, to provide a sensor array that can, if required, conform or is conformable in shape and arrangement to the inside wall of an elongate hollow housing including an elongate body with a head end, an inserted end, and an outer surface being continuously tapered from the head end to the inserted end.

There are practical reasons for using a substantially circular cross-section for the hollow elongate sensor housing but there are no substantially detrimental reasons that the housing should only be substantially circular in cross-section, e.g. the shape maybe square or rectangular or even triangular in cross-section along the full length of the hollow elongate sensor housing, there will however be some difficulty in creating a conforming shape in the soil to be characterised/measured by the soil sensor arrangement inserted into the elongate hollow housing.

In a broad aspect there is provided a sensor array for use in a hollow elongate housing having a continuously tapered outer wall having a larger maximum outer diameter at a first end compared to the maximum outer diameter of a second end for use in the ground, the sensor array element includes: a carrier sheet of flexible material, the carrier having at least two pairs of electrically conductive regions lying between an first edge and a second edge of the carrier sheet, the two electrically conductive regions of a pair of electrically conductive regions are shaped and located near enough each other such that when the carrier sheet is formed into a shape and inserted into the elongate hollow housing the pair of electrically conductive regions form a capacitive element, and adjacent pairs of capacitive elements have a different diameter, each usable to sense at least the moisture content of the ground surrounding the location of the capacitive element located within the elongate hollow housing.

The sensor array wherein the capacitive elements, when within the elongate hollow housing, have a common central axis that is co-axial with other of the capacitive elements located within the elongate hollow housing.

Further aspects of the sensor array element may include:

At least one pair of opposite edges of the carrier sheet is non-parallel.

That the conductive regions extend from the first edge to the second edge.

There being a centralising arrangement associated with the carrier sheet having at least three contacts with the inner wall of the elongate hollow housing for centralising the carrier sheet with the housing.

The centralising arrangement includes deformable portions of the carrier sheet arranged to project radially outward, when the material is shaped for insertion into the elongate hollow housing, to contact the inner wall of the elongate hollow housing and centralise the formed shape within said elongate hollow housing.

The at least three contacts are substantially evenly radially spaced.

One edge of the carrier sheet includes fixing elements to attach that edge to the carrier sheet when the carrier sheet is formed into a shape suitable for insertion into the elongate hollow housing.

The carrier sheet can conform to the shape of the inner wall of said elongate hollow housing.

A fixing element includes a tang formed by the shape of the flexible material of the carrier sheet being suitable for insertion into a slot in the carrier sheet and for resisting extraction from the slot in the carrier sheet.

In one aspect the tang has a length and a portion of the tang has a greater width at a free end than the rest of the tang, the carrier sheet having one or more slots located such that when the inserted end of the tang is inserted in the slot the formed carrier sheet has a predetermined diameter at the location of the slot.

The tang arranged to project laterally from an edge of the carrier sheet.

There being multiple slots in the carrier sheet, the slots located such that when a respective tang is inserted into the slot located closer to the edge of the carrier sheet opposite the edge from which a tang projects the predetermined diameter at the location of tang and slot of the formed shape is the largest compared to the use of other slots.

Portions of the carrier sheet are deformable to project radially outward, wherein when the material is shaped for insertion into the elongate hollow housing, and when the carrier sheet is located within the elongate hollow housing, the radially outer extremity of the portions of the carrier sheet contact the inner wall of the housing to centralise the formed shape within said elongate hollow housing. This also assists in making adjacent sensor arrays to be co-axial when located in the hollow elongate housing.

There being at least two pairs of conductive regions wherein each pair is at least one capacitive element of a tuned circuit.

There being three pairs of conductive regions on a carrier sheet.

In an aspect the carrier sheet has three pairs of conductive regions wherein each pair of conductive regions forms a different maximum outer diameter capacitive element each being at least one capacitive element of a respective tuned circuit.

An end of each conductive region is adapted to be electrically conductively connected to a circuit board.

That the same size carrier sheet can be used within the housing, the carrier sheet having multiple slots and multiple tangs, the tangs usable for engagement with respective slots to provide successively smaller diameter shaped carrier sheets along the length of the carrier sheet when shaped suitable for insertion into the elongate hollow housing, such that multiple carrier sheets are locatable along the length of the elongate hollow housing from the first end to the second end of the elongate hollow housing.

In a broad aspect there is provided a sensor for use in the ground which may include, a elongate hollow housing having a continuously tapered outer wall having a larger maximum outer diameter at a first end compared to the maximum outer diameter of a second end for use in the ground; a sensor circuit including at least a portion of a tuned circuit requiring a capacitive element, the circuit mounted to a circuit board that occupies a portion of the hollow elongate housing; and a carrier sheet of flexible material, the carrier having at least two pairs of electrically conductive regions lying between an first edge and a second edge of the carrier sheet, the two electrically conductive regions of a pair of electrically conductive regions are shaped and located near enough each other such that when the carrier sheet is formed into a shape and inserted into the elongate hollow housing the pair of electrically conductive regions form a capacitive element, and adjacent pairs of capacitive elements have a different diameter, each usable to sense at least the moisture content of the ground surrounding the location of the capacitive element located within the elongate hollow housing.

In a further broad aspect there is a sensor array for use in an elongate hollow housing having a larger outer diameter at an first end than the second end, the sensor array includes: a sensor circuit including at least a portion of a tuned circuit requiring a capacitive element, the circuit mounted to a circuit board having at least two circuits and the circuit board adapted in size to occupy a portion of the elongate hollow housing; and a carrier sheet of flexible material, the carrier having at least two pairs of electrically conductive regions lying between an first edge and a second edge of the carrier sheet, the two electrically conductive regions of a pair of electrically conductive regions are shaped and located near enough each other such that when the carrier sheet is formed into a shape and inserted into the elongate hollow housing the pair of electrically conductive regions form a capacitive element when connected to the circuit, and adjacent pairs of capacitive elements have a different diameter, each usable to sense at least the moisture content of the ground surrounding the location of the capacitive element located within the elongate hollow housing.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

The reference to any background or prior art in this specification is not, and should not be taken as, an acknowledgment or any form of suggestion that such background or prior art forms part of the common general knowledge.

Specific embodiments will now be described in some further detail with reference to and as illustrated in the accompanying figures. These embodiments are illustrative, and not meant to be restrictive of the scope of the disclosure herein. Suggestions and descriptions of other embodiments may be included but they may not be illustrated in the accompanying figures or alternatively features may be shown in the figures but not described in the specification.

DETAILED DESCRIPTION OF EMBODIMENTS

Figure 1:
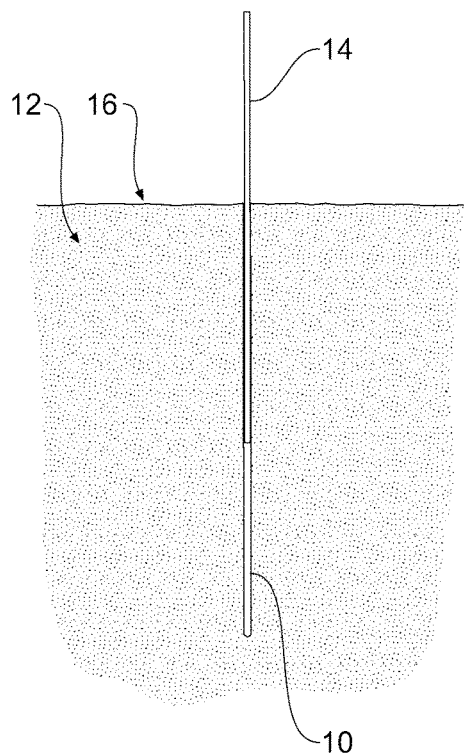
FIG. 1 depicts the partial insertion of an elongate sensor housing into the ground.
Figure 2:
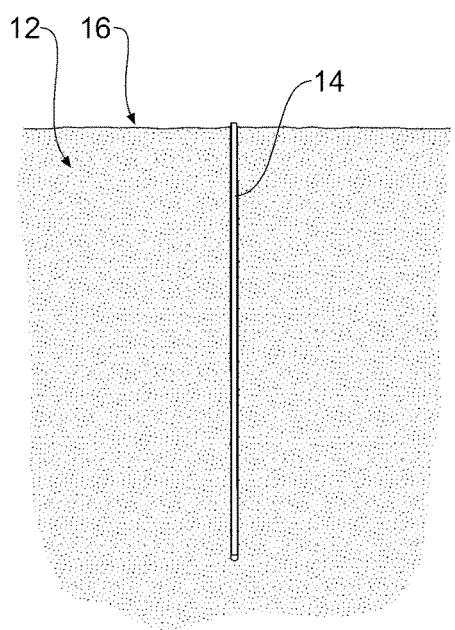
FIG. 2 depicts the complete insertion of an elongate sensor housing into the ground.

FIGS. 1 and 2 illustrate the result of the formation of an opening 10 (FIG. 1) into the ground 12 using an auger having tapered fighting. Such an auger is usable for creating an opening in the ground suitable for the insertion of an hollow elongate sensor housing 14 (FIG. 1) where the elongate hollow sensor housing has an outer shape that is circular in cross-section having a smaller diameter at the inserted end relative to the non-inserted end (head end) of the elongate hollow sensor housing. The hollow elongate housing has a continuously tapered outer wall having a larger maximum outer diameter at a first end compared to the maximum outer diameter of a second end for use in the ground. The hollow elongate sensor housing is pushed into the prepared opening until a datum line on the outside of the elongate housing (not visible in FIG. 2) reaches the ground level 16 at which time the full tapered length of the elongate housing is located within the prepared opening. In one embodiment the datum will be at the top of the housing, which can be aligned with the top of the soil. In one arrangement the housing can be stood on by the installer to place the elongate housing firmly into the prepared opening until the top of the elongate housing is level with the ground level.

It will be noted that FIG. 2 shows that undisturbed ground 12 surrounding the elongate sensor housing is in contact with the whole outer surface of the elongate sensor housing 14. This is the ideal condition for maximising the effectiveness of the sensors arranged in an array within the elongate hollow sensor housing, which are in one embodiment, located every 10 cm along the full length (depth when installed) of the elongate hollow sensor housing (not all shown to de-clutter the figure) thus providing a means to record at least soil moisture and other characteristics of the soil in the location of the elongate hollow sensor housing along the depth of the prepared opening 10 in a field of growing crop (not shown to de-clutter the figures).

The lack of air spaces and gaps, in particular, between the outer surface of the elongate hollow sensor housing and the surrounding ground is substantially avoided. The avoidance of such gaps ensures that when there is a rain event, water does not collect within the gaps or create preferential water flow paths down the outside of the sensor, this would tend to distort any sensor measurements. The tapered outer shape of the elongate hollow sensor housing and the prepared opening thus conform, since the two shapes correspond before the insertion of the sensor and become conforming (or is conformable) as the elongate hollow sensor housing meets the surface of the soil. In prior soil sensor installation arrangements the prepared opening and the hollow elongate sensor housing may have corresponded (in that they were both cylindrical) but no amount of downward pressure would improve the conformance of the outer surface of the hollow elongate sensor housing and the wall of the prepared opening. Indeed the need to maintain the cylindrical form of the opening could not be consistently achieved, whereas the above described use of a tapered auger to create a tapered opening for the tapered hollow elongate sensor housing provides for self-conformance of the hollow elongate sensor housing to the inner wall of the prepared opening.

The hollow elongate sensor housing has an outer diameter (since in this embodiment it has a circular cross-section) that is X at the head end (that end which is at or about ground level) which is greater that the outer diameter Y at the inserted end. In one embodiment, the taper is about 6 mm over a length of about 1200 mm where X is 24 mm and Y is 30 mm to form a body adapted for housing a soil moisture sensor arrangement.

In a further embodiment, the body of the hollow elongate sensor housing has a flexible form into which a flexible form of sensor array element is located. The flexible sensor array element is formed in one embodiment from plastic sheet material which can be folded or at least deformed to be passed through an aperture in the flexible form of the body and have some resilience and tendency to conform to the preferably rounded tapered inner wall of the flexible body and when located appropriately along the internal length of the body ready to be connected as required with other sensor array elements to form an array and connected to a circuit which is part of the sensing electronics. The capacitive element and in one example a tuned circuit are usable to sense at least the moisture content of the environment surrounding the location of the capacitive element located within the elongate housing. The overall sensor circuit includes at least a portion of a tuned circuit requiring a capacitive element, where the circuit is mounted to a circuit board that occupies a portion of the hollow elongate housing. It should be understood that while sensor array elements are generally described and discussed herein as parts of an array of multiple elements, single elements or a plurality of elements may be used in embodiments of the disclosure, without departing from the scope thereof. An overall sensor circuit as described herein may comprises a single sensor array element, or multiple sensor array elements, without departing from the scope of the disclosure.

Figure 5:
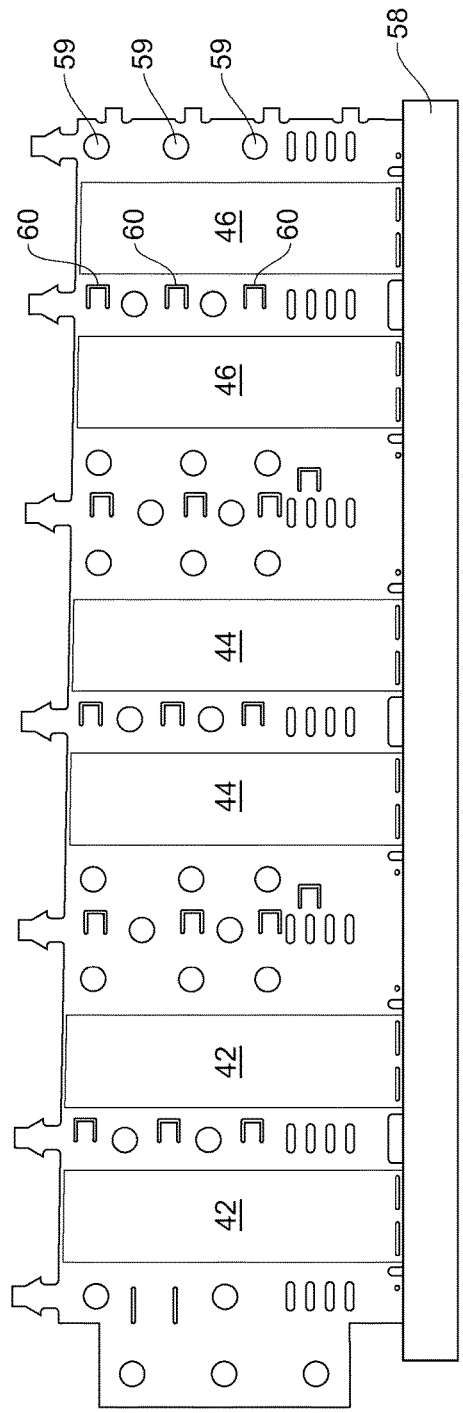
FIG. 5 depicts the flexible sensor in the form of a carrier sheet connected to a printed circuit board.

The circuit as depicted in FIG. 5 is incorporated into a printed circuit board having a combination of surface mount discrete components and integrated circuits, but it is possible for the circuit to be incorporated into the carrier sheet material and so the term "connectable" also includes the situation where the capacitive elements are directly electrically connected to the circuit which is incorporated into/onto the carrier sheet material.

The connection of the conductive regions to the printed circuit board 58 is depicted in FIG. 5 as occurring at the edge of the carrier sheet to which the conductive region extends, but, as described elsewhere the conductive region incorporated with the carrier sheet may only extend between the sides but not extend to the edge of the carrier sheet, so the connectability may require other ways to make the electrical connection, such as for example, a wire bus, a band of conductive material, positioning of the printed circuit board over a portion of the carrier sheet or a portion of the printed circuit board extending across a portion of the carrier sheet, and many other alternatives that will be appreciated by those of skill in the relevant art.

The capacitive element and tuned circuit and associated signal processing circuit and computer processor may locally store the soil moisture measurements (data) made over time. The circuit may also be connectable or connected to a communication arrangement, to permit data collected to be communicated elsewhere for processing in some further way, typically for presentation of soil moisture profiles in the surrounding soil and for displaying those profiles as they change over time due to rain, watering and other environmental events and as soil moisture is taken up by the crop in the soil.

The capacitive element and circuit and associated signal processing circuit may be set up to determine soil moisture content by sensing the voltage, the frequency or phase, the current, or other parameters such as period of a generated signal having a referenced source.

Soil moisture is not the only type of data measured by the circuits, and can include, salinity (using the same capacitive elements), temperature, etc.

In a further embodiment, the sensor array element is formed on a flexible carrier, such as a plastic sheet, and the sensor array can be wrapped into a substantially tapered cylindrical shape over a similarly substantially circular cross-section elongate former (solid or hollow) which can be housed within a housing of the form described herein.

The mention of circular cross-section is exemplary only, as the shape of the sensor need not be circular to perform its sensing task, although in one embodiment the sensor conforms to the inner wall shape of the housing wherein the outer wall shape is the same as the inner wall shape in cross-section so that the sensor is located so as to be in close proximity to the soil in which the housing is inserted.

Further the sheet of flexible carrier material may include regions of reduced flexibility or be substantially inflexible for reasons, such as assistance to conform to an irregularly shaped inner wall of a housing (which may in other embodiments be non-circular in cross-section), for fitment of circuits and other sensors and the like within the hollow elongate housing, or to support portions of a sensor array not included on the carrier.

In yet another form, the flexible sensor carrier is inserted in the hollow elongate housing and positioned adjacent the inner wall of the housing, which is substantially circular in cross-section. Adjacency can mean that the flexible sensor carrier is spaced from the inner wall but still has much the same cross-sectional shape as the inner wall. In one embodiment, the spacing is provided by non-conductive spacer tangs located randomly or in an ordered grid radially about the carrier between the carrier and the inner wall. The spacers can be integrally formed in the carrier or added to the carrier.

In one embodiment, the inside of the elongate housing can be filled with material once the sensor array element is inserted, so as to fix the element and other apparatus and including the spacers when suitably located within the housing. The filling material is electrically non-conducting and will when processed or after self-setting, contribute to the stiffening of the housing and more importantly the flexible sensor carrier and hence the sensor areas carried thereon are fixed in location relative to each other and the housing, thus ensuring the electrical and electromagnetic characteristics will be maintained over time, during calibration and beyond such as during transportation, storage and repeat use in the field.

In yet another form, the flexible sensor carrier is positioned adjacent a printed circuit board (PCB) and connected thereto. The PCB is made of a non-conductive substrate on which conductive tracks and pads are etched, typically using copper to become a printed circuit board assembly. The tracks and pads are connected to discrete and integrated circuit elements to form an electronic and electrical circuit. At least some of the tracks and pads are located adjacent an edge of, in this embodiment the elongate PCB, so that they can be easily electrically connected to appropriately located electrically conductive regions on the flexible sensor carrier.

In an embodiment, the inner wall of the housing is substantially circular in cross-section, and the flexible sensor carrier substantially conforms to the shape of the inner wall of the housing. Thus, the electrically conductive regions carried by the carrier will also conform to the outer wall shape of the hollow elongate sensor housing; although the sensor element may not lie in contact with the inner wall (the mechanism to achieve this is to be described later using an embodiment of the flexible sensor carrier). The overall sensor circuit includes the flexible sensor carrier having a capacitive element thereon being a portion of a circuit, where the rest of the circuit is incorporated into a circuit board that occupies a portion of the hollow elongate housing.

Figure 4:
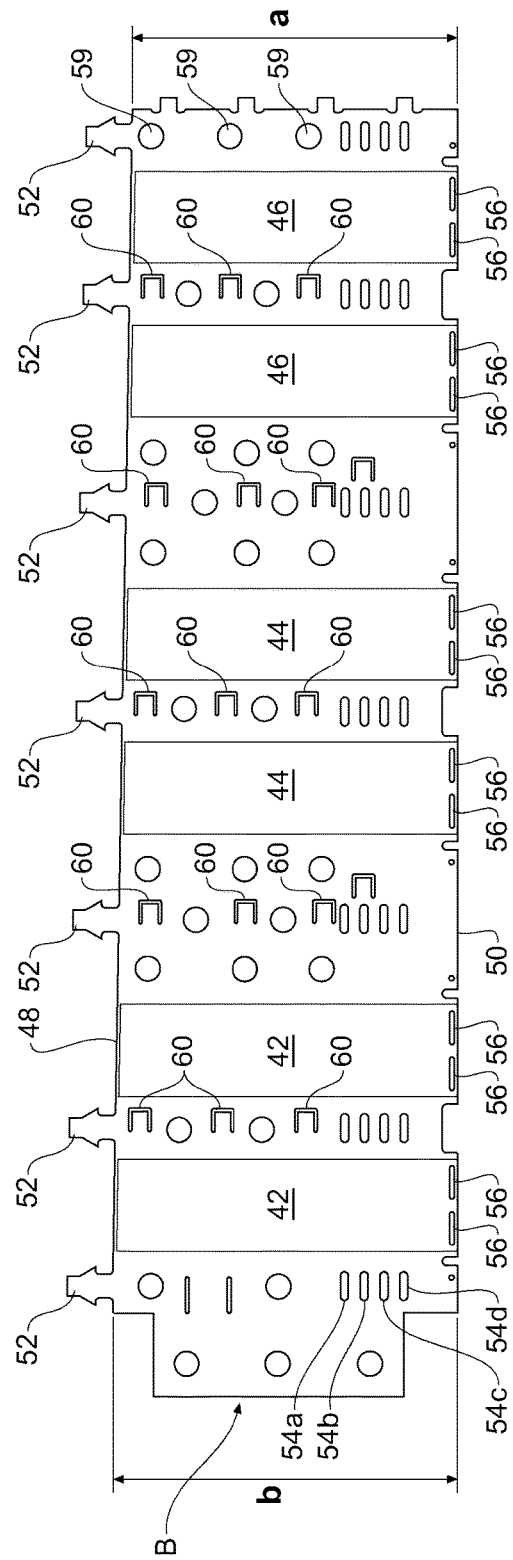
FIG. 4 depicts a plan view of an embodiment of the flexible sensor in the form of a carrier sheet.

In one embodiment, the inside of the hollow elongate sensor housing can be filled with, such as for example, polyurethane, material which sets over time and becomes solid, so as to fix the sensors and other apparatus in location within the housing. FIGS. 4 and 5 depict holes 59 which allow the flow of flowable material through the flexible carrier sheet and so that it completely surrounds the carrier sheet without unduly distorting the carrier sheet and which will, when the material has set, provide additional stiffness to the existing tensile strength of the carrier sheet material and the circuit board which will run the internal length of the hollow housing.

The inside of the housing will thus contain appropriately positioned sensor/s, which are at the same time connected with a respective sensor PCB circuit board and those circuits are arranged to communicate their respective signals or collected measurement data and sometimes processed data, external of the housing (possibly by wired connection/s but preferably wireless connection, both not shown).

Figure 3:
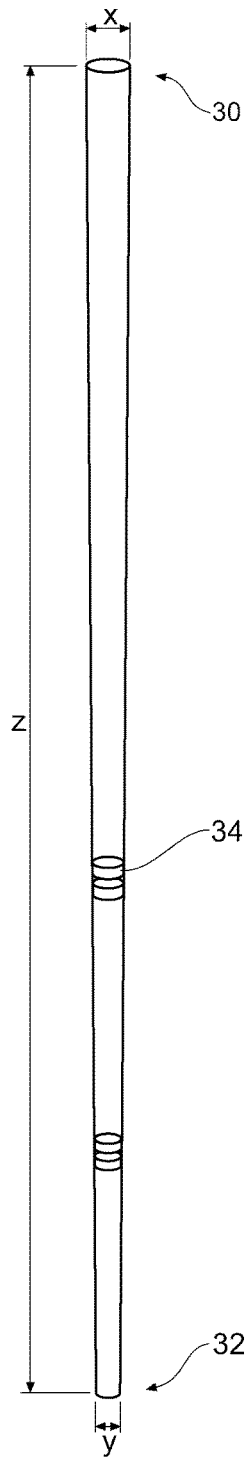
FIG. 3 depicts a pictorial representation of a elongate tapered sensor housing in partial cross-section depicting capacitive sensors located along the length of the elongate hollow housing.

The body of the housing 14 having a head end 30 and an inserted end 32, the body shaped so that the maximum outer diameter of the extremity of the inserted end is smaller than the maximum outer diameter of the head end of the body, in this embodiment x=30 mm and y=24 mm and the length z of the housing is 1200 mm. The outer shape of the body is continuously tapered in outer shape for ease of insertion of the inserted end into a prepared opening 10 in the soil (FIG. 1), in that there is generally a frustoconical shape and where the external wall of the housing is generally circular in cross-section, as is pictorially depicted in FIG. 3. For illustrative purposes the sensor elements depicted in FIG. 3 are shown without adjacent sensor elements, as will be described in this specification, being on the same carrier sheet.

FIG. 4 depicts a plan view of an embodiment of the flexible sensor carrier sheet. The rear of the sheet is not shown in any of the Figures since it is not different in visual appearance, showing because of the transparency of the sheet material the dark regions where the conductive film is located and the various apertures (slots, holes, etc.) as would be apparent from the plan view.

When referring to the carrier sheet there is no special connotation of the term "carrier" since in the embodiment the electrically conductive regions are encapsulated within the sheet like material but in another embodiment the electrically conductive regions could be formed on the outside of the sheet material. The sheet need not be a single sheet of material, a sheet for use in the embodiments described herein may be formed from two or more sheets, in one further example, one sheet overlaying the other to form an encapsulation of the conductive regions, in such an embodiment, protecting them from environmental effects and in another embodiment, one sheet is located on one side of the conductive region and a portion of a sheet is located on and over the other side of the conductive region.

The carrier sheet 40 has four edges and is made of flexible non-electrically conductive material formable, for example FPC having a thickness of 0.177±0.03 mm. The flexibility of the carrier sheet allows it to be folded into a shape, which conforms to the shape of the inner wall of said elongate housing prior to insertion and once inserted may further adapt to the inner wall shape.

The carrier sheet has electrically conductive regions (as shown in FIG. 4) that can be made by coating the carrier sheet with, in one embodiment a film of conductive material such a electrolytic copper) wherein pairs of conductive regions 42, 44, and 46 are arranged along the length of the carrier sheet. The regions that make up the pairs are shaped and located near enough each other to form, when the material is shaped, the capacitive element of a tuned circuit (not shown). The proximity of two such regions is arranged to create a capacitor working with a respective tuned circuit the details of at least one circuit of this type are provided in the field of elongate soil sensors and in particular at least one of the patents/patent applications incorporated by reference earlier in this specification. In one embodiment, the conductive region is made of a base material, being 1 oz electrolytic copper on one side of the carrier sheet 3 mil PI, and adhered to the carrier sheet using 17μ of glue. The solder mask cover layer is 1 mil PI, 25μ glue Surface finish: ENIG.

The carrier has at least two pairs of electrically conductive regions lying between a first edge and a second edge of the carrier sheet. This description includes the electrically conductive regions extending from one edge to the other edge, which is depicted in FIGS. 4 and 5, but there can be a positioning of the electrically conductive region from one side to part way to the other side or in another embodiment the electrically conductive region may start a distance from one side and end a distance from another side. The length of the conductive region may be sufficient so that the regions overlap when the carrier is shaped to fit within the hollow elongate housing. Yet further the pairs of conductive regions may vary in length so that adjacent pairs of conductive regions have different lengths.

Two electrically conductive regions of a pair of electrically conductive regions are shaped and located near enough each other such that when the carrier sheet is formed into a shape and inserted into the elongate hollow housing the pair of electrically conductive regions form a capacitive element. In one embodiment, as depicted n FIGS. 4 and 5 adjacent pairs of capacitive elements have a different diameter when the carrier sheet is shaped to have a tapered cylindrical shape for insertion into the hollow elongate housing at a suitable location along the internal length of the housing. In another embodiment the length of the electrically conductive regions of each pair define the formed diameter of the capacitive element when the carrier sheet is shaped for insertion into the hollow elongate housing.

Each pair of electrically conductive regions forming a capacitive element are usable to sense at least the moisture content of the ground surrounding the location of the capacitive element located within the elongate hollow housing since they can be made part of a sensor circuit designed to use the capacitance of the capacitive element, as described in the reference patents and patent applications and described in this specification.

Figure 6:
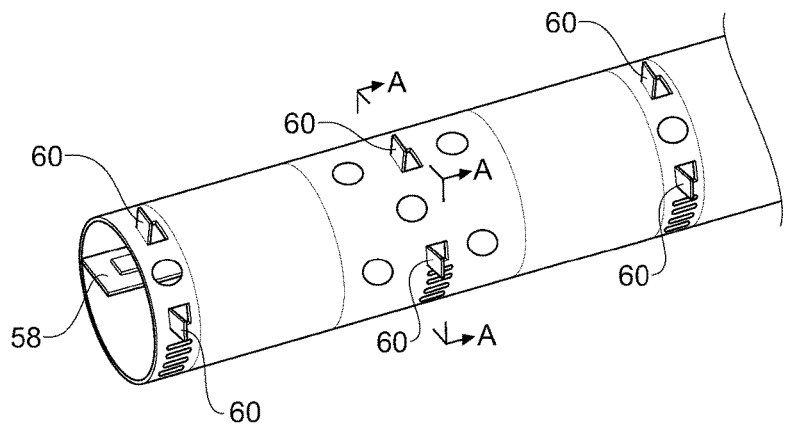
FIG. 6 depicts a perspective view of the flexible sensor in the form of a carrier sheet while connected to a printed circuit assembly in a folded and fixed state wherein the carrier sheet has a substantially circular cross-section.
Figure 7:
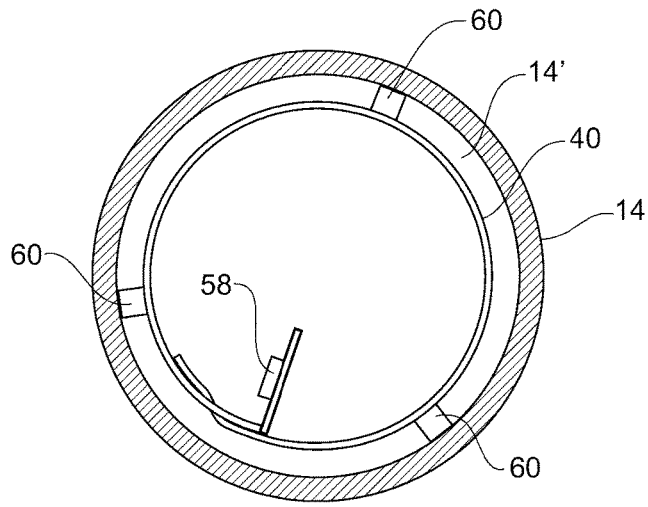
FIG. 7 depicts an end view of the flexible sensor in the form of a carrier sheet while connected to a printed circuit assembly in a folded and fixed state having a substantially circular cross-section.
Figure 8:
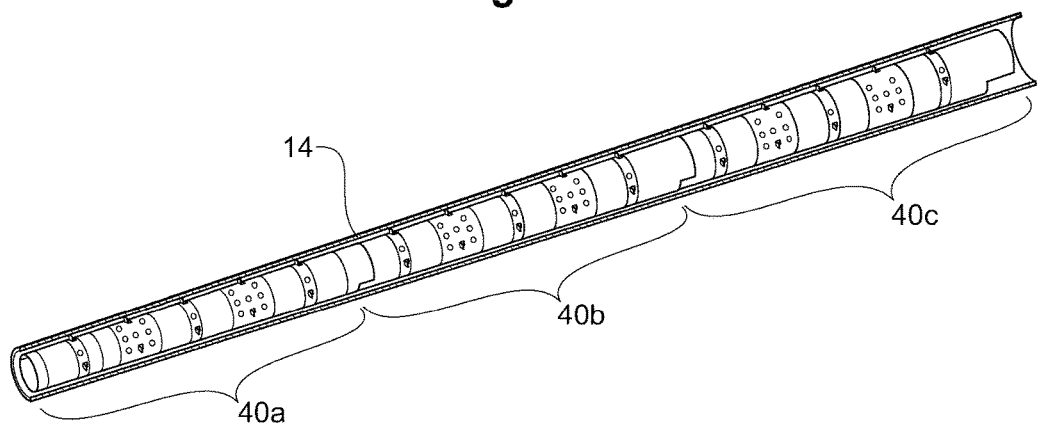
FIG. 8 depicts a perspective view of the flexible sensors in the form of carrier sheet and associated printed circuit board or boards arranged along the full internal length of a cut-away view of the tapered elongate hollow sensor housing.

One embodiment of the folded shape of the carrier and formed capacitive elements will be more apparent when viewing FIGS. 6, 7 and 8, as being substantially circular in cross-section. The capacitive elements, when within the hollow elongate housing, can in one embodiment, have a common central axis that is co-axial with other of the capacitive elements located within the housing as well as other shaped carrier sheets also having two or more capacitive elements.

It is possible to have a carrier sheet with just one pair of electrically conductive regions and further for that carrier sheet to be shaped when formed to have a different diameter at its ends, for use in a single hollow elongate sensor housing that is tapered. Such a use is possible when using such a sensor in turf, which does not have a root system much deeper than 10 cm to 30 cm.

The pairs of conductive regions form a capacitive element of a tuned circuit when connected to such a circuit. The conductive regions are in effect capacitive rings as described in the referenced patents incorporated by reference. There can be multiple pairs of conductive regions provided on the carrier sheet and in this embodiment there are three pairs of conductive regions, thus the ability to form three capacitive element and each pair of conductive region is adapted to be electrically conductively connected to a circuit board. This connection is preferably in the form of solder but may be mechanically and electrically achieved by additional elements, such as for example, a clamp formed on the circuit board to accept the end of the conductive region. The long apertures 56 shown on FIGS. 4 and 5 act as a well for the solder when the end of the conductive region are used to electrically connect the conductive regions to the tuned circuit located on the circuit board using solder. Each pair of conductive regions forms a different diameter conductive region as part of the respective tuned circuits.

In this embodiment there are three pairs of conductive regions incorporated with the carrier sheet wherein each pair of conductive regions forms a different maximum outer diameter capacitive element each being at least one capacitive element of a respective tuned circuit.

In an embodiment an end of each conductive region is adapted to be electrically conductively connected to a circuit board but each end may be so adapted.

Of particular note is that the plan view shape of the carrier sheet as depicted in FIG. 4 is not a rectangular shape but rather, as depicted, the top edge 48 is not parallel to the bottom edge 50 thus at least one pair of opposite edges is non-parallel. The slope of one edge relative to the other edge of the pair is such that the distance from the bottom edge to the top edge is smaller on the right hand edge 'A' than the left hand edge 'B'. This configuration allows for the carrier sheet to have a smaller diameter on the right hand side than the left hand side when folded into the substantially circular cross-sectional shape, and thus capable of having conformance to the inner wall of the housing described.

It may be possible to form the carrier sheet into a partially conical shape so as to conform substantially with the inner wall shape of an elongate hollow housing. It may also be that one or more edges of the sheet are shaped to eliminate or minimise the overlap of sheet material at one or both ends so as not to interfere with an adjacent carrier sheet similarly formed but having a matching diameter at the region of adjacency increasing or decreasing along its length away from that region of adjacency. This arrangement is not ideal and may require that each sheet have a different shape thus making the manufacture of the sheets more expensive as well as the manufacture of a soil moisture sensor within a suitable housing since the adjacency and hence spacing may be adversely affected as will be the additional ordering of the elements before construction of the arrangement.

The fixing of the carrier sheet in a folded shape is achieved, in this embodiment, by the use of fixing elements in the form of tangs and slots wherein the tang is shaped to be insertable to the slot but resist extraction from the slot in the carrier sheet, but the fixing could be achieved in a number of other ways, for example, tabs and fixing elements such as a staple, or glue, or rivet, etc. associated with appropriate positional markings being located on the sheet. In an embodiment, one edge of a pair of opposite edges of the carrier sheet includes using a fixing element to attach that edge to the carrier sheet when the carrier sheet is formed into a shape to conform to the shape of the inner wall of said elongate housing. The fixing element may be used at locations not associated with an edge of the carrier sheet as long as the shape is maintained for insertion and after insertion into the hollow elongate housing.

In an embodiment, the fixing element includes a tang or tangs 52 located along the edge 48 of the carrier sheet, as depicted in FIG. 4. A tang is arranged to project laterally from the edge 48 of the carrier sheet and on some cases one such tang (fixing element) may suffice but in the embodiment depicted in FIGS. 4 and 5 multiple tangs are shown and used.

It will be noted that the any use of the relative terms upper, lower, right hand and left hand sides are all with respect to the orientation of the carrier sheet as depicted on FIG. 4, but that it will be understood that such terms are relative and not meant to be limiting.

The tangs have a particular shape that has a length and a portion of the tang having a greater width at a region than the rest of the length of the tang. In this embodiment the tang has an arrow head shape incorporated into it, which because the material is flexible, the side apexes of the arrow are capable of being slightly distorted such that the arrow head can be inserted into an aperture of slightly less width but be resistant to extraction from the slot in the carrier sheet. In this embodiment the carrier sheet has one or more slots located such that when the tang is inserted in the slot the formed carrier sheet has a predetermined diameter (not exact diameter since there is some length of the shaft of the tang below the arrow head and the side of the sheet) at the location of tang and slot of the then formed shape. However, the diameter of the sheet in the region of the inserted and captured tang has a maximum diameter. Therefore, the conductive regions will form a conductive ring made-up of an overlap of the conductive region lengthwise which from an electromagnetic perspective is a ring like any other conductive ring, which has a physical size partly determined by the predetermined diameter. Note that two adjacent rings form the capacitive element of the tuned circuit of the sensor array element so their combined electrical and electromagnetic characteristics are the result of the configuration described.

Slots 54a, 54b, 54c, and 54d are located in the carrier sheet such that when a respective tang is inserted into the slot located closer to the edge of the carrier sheet the edge 48 of the carrier sheet, the diameter at the location of tang and slot of the formed shape is the smallest compared to the use of other slots. In an embodiment there are multiple slots in the carrier sheet, the slots being located such that when a respective tang is inserted into the slot located closer to the edge of the carrier sheet opposite the edge from which a tang projects, the predetermined diameter at the location of tang and slot of the formed shape is the largest compared to the use of other slots.

It is noted in FIGS. 4 and 5 that the tangs are aligned with each other (running generally parallel to the edges A and B of the carrier sheet and opposite a respective tang). However, in another embodiment, it could be that successive slots are displaced sideways with respect to each other and the respective tang, in such a manner that when a tang is inserted into a slot in the carrier sheet, the carrier sheet not only forms a substantially circular cross-sectional shape at that location it also miss-aligns the otherwise (in one embodiment) parallel opposite edges of the sheet and in this embodiment the edge from which the tang projects, such that the shape of the carrier sheet is also tapered from one end to the other. In this embodiment (not shown) there can beneficially be more than one tang and respective slot used to form the described shape.

Multiple of the same size carrier sheet can be used within the housing. The carrier sheet having multiple slots and multiple tangs, the tangs are usable for engagement with respective slots to provide successively smaller tapered shaped carrier sheets along the length of the carrier sheet when shaped suitable for insertion into the elongate hollow housing. Thus, multiple carrier sheets are locatable along the length of the elongate hollow housing from the first end to the second end of the elongate hollow housing.

With reference to FIGS. 4 and 5, use of slot 54*a* will create the smallest diameter while use of slot 54*d* will create the largest diameter. A similar displacement of the tangs in the embodiment described in the previous paragraph will have a similar effect. Referring again to the embodiment depicted in FIGS. 4 and 5, since edge A is shorter than edge B the diameter of the shaped sheet will vary along its length from smaller to larger when respective tangs are used and thus substantially conform to the shape and diameter of the inner wall of the internally tapered housing. The slots are located adjacent the opposite edge of the carrier sheet to the edge from which the tangs project. Once the tangs are engaged with their respective slots the diameter of the respective conductive regions has been set at the location of the tang and slot and since the tangs project from an edge which is non-parallel to the edge aligned with the slots, then the diameter of the carrier sheet is different along the length of the carrier sheet and in essence the carrier sheet tapers from one edge to another being the edges A and B depicted in FIG. 4. The diameter at the location of each tab insertion is maintained during the process of filling the housing with settable material and thus the electrical and electromagnetic characteristics of the capacitive elements, which are part of the sensor array element, are also set.

When reference is made to the diameter of a folded carrier sheet it is appreciated that the folded carrier sheet has a progressively reducing diameter along its length because of the non-parallel opposite sides of the carrier sheet on which the tangs are located, but it is reasonable to do so since the smallest diameter of a shaped carrier sheet has been configured to be about the same as the largest diameter of an adjacently located carrier sheet within the tapered housing, so that the average diameter of adjacent shaped carrier sheets will thus be larger or smaller accordingly.

In an embodiment not depicted the carrier sheet is square or rectangular and as described elsewhere the conductive regions are shaped and sized to allow the formed shape of the carrier to create pairs of capacitive elements with suitable capacitive characteristics but the carrier sheet when shaped forms a tapered carrier sheet insertable into a hollow elongate housing. Thus if the carrier sheet is to have a square of rectangular shape, the tapered shape can still be formed by using slots located in the carrier sheet so that the formed diameter is smaller at one end of the formed sheet that the other. This embodiment is not shown in any of the figures but is a readily achievable alternative with the knowledge that the formed carrier sheet will have an extension of an apex of the sheet at both ends which may interfere with an adjacently located formed carrier sheet when located within the hollow elongated housing.

Using the tangs in respective slots to provide a smaller or larger graduated diameter shaped sensor array elements it is possible to use multiple of the same basic carrier sheet to provide all the required sensor array elements within the hollow elongate housing. Thus the shaped carrier sheet having an overall greater graduated diameter (tapered shape) is positioned at the larger (inner and outer) diameter end (head end) of the tapered housing while progressively smaller graduated diameter shaped carrier sheets are used along the internal length of the hollow elongate housing from the head end to the inserted end of the housing.

In an embodiment, a sensor array is for use in an elongate hollow housing. The housing having a larger outer diameter at a first end than the second end. In an embodiment, the sensor array includes a sensor circuit including at least a portion of a tuned circuit requiring a capacitive element, wherein the circuit is mounted to a circuit board having at least two circuits and the circuit board is adapted in size to occupy a portion of the hollow elongate housing. The sensor array also including a carrier sheet of flexible material where the carrier has at least two pairs of electrically conductive regions lying between a first edge and a second edge of the carrier sheet. The two electrically conductive regions of a pair of electrically conductive regions are shaped and located near enough each other such that when the carrier sheet is formed into a shape and inserted into the elongate hollow housing the pair of electrically conductive regions form a capacitive element. The capacitive element when connected to the circuit provides at least a part of a tuned circuit, and adjacent pairs of capacitive elements have a different diameter, each usable to sense at least the moisture content of the ground surrounding the location of the capacitive element located within the elongate hollow housing.

FIG. 5 depicts the positioning of a Printed Circuit Board (PCB) 58 (no discrete or integrated circuit elements are shown), although it should be noted that there is a circuit associated with each pair of conductive regions, part of which is an incomplete tuned circuit (requiring the attachment of the capacitive elements formed by the conductive regions of the flexible carrier sheet as described previously) along the edge 50 of the carrier sheet as depicted in FIG. 4 to form a capacitive sensor. Details of circuits which could be used are provided in the referenced patents.

In one embodiment depicted, each conductive region has, at least one slot 56, and surrounding the slot is exposed electrically conductive material, so that an electrically conductive connection can be made to the PCB and in particular to a tuned circuit. The preferable connection is by way of the use of solder, but there can be other ways to achieve the electrical connection with the slot also capable of being mechanically engaged in addition to the electrically conducting connection required for the tuned circuit to be completed.

Once the carrier sheet is appropriately connected to the PCB 58 the carrier sheet can be shaped so that the tangs engage with the appropriate slots and the shape will become similar to that depicted in FIGS. 6 and 7 (cross-sectional view of FIG. 6).

A further feature of the arrangement is the use of portions of the non-electrically conductive carrier sheet which are deformable to project radially outward such that when the material is shaped the radially outer extremity (in this embodiment the free end of a tab but in other embodiments the shape of the portion may be different but will still have a radially outer extremity) of the portions lies against the inner wall of the hollow elongate housing and the formed carrier sheet is substantially centralised within the housing, thus being centralised by a centralising arrangement, pictorially represented by FIG. 7, which depicts a cross-section of a sensor array (40 and 58) in a formed state located with a housing 14 having an inner wall 14'. This also assists in making adjacent shaped sensor arrays co-axial when located in the hollow elongate housing.

The portions, in this embodiment, tabs 60 are located radially about the outer surface of the carrier sheet. In a preferred arrangement the tabs 60 are created by the tab shape being cut by a die and are then hand or machine manipulated to project outwards relative to the longitudinal central axis of the formed shape of the sensor array. Ideally the tabs 60 are manipulated to be bent greater than 90 degrees relative to the carrier sheet and using the resilience of the material of the carrier sheet, the tabs will then be biased to adopt an approximately 90 degree orientation to the carrier sheet at its radial location. The direction of the tab in this condition is such that the carrier sheet is inserted into the housing in a particular direction and the tab then actively by way of its resilience ensures that the carrier sheet is centralised within the housing. There are three tabs depicted in the side view in FIG. 7 since there are three tabs 60 shown in a line across the carrier sheet on FIGS. 4 and 5, which are approximately 120 degrees radially apart when the sheet is formed for insertion into the elongate hollow housing thus creating three contacts with the inner wall of the hollow elongate housing for centralising the carrier sheet within the hollow elongate housing. Five such lines of tabs are depicted in FIGS. 4 and 5 to allow for the creation of five sets of three tabs to assist in the centralising of the sensor array element. However there could be more such tabs 60 in a set, and unlikely to be less, since two such tabs alone would not have the desirable effect of centralising the sensor array within the inner walls of the housing. There could for example, be two such tabs or similar arrangement, and there could be a projection from the PCB that protrudes through a provided aperture in the carrier sheet to provide one of at least three contact points (again ideally, evenly radially spaced, e.g. approximately 120 degree radial separation) to achieve the centralising of the array of sensors in the vicinity of the three point centralising arrangement. The tabs also allow for any unevenness of the internal walls of the housing to not affect the shape of the capacitive elements carried by the carrier sheet, while still providing a centring of the shaped flexible material when located in the housing.

FIG. 8 depicts a cut-away view of an elongate housing 14 within which is located multiple formed carrier sheets 40a, 40b, and 40c. The illustration is not to scale as the length is not representative of the diameter at either end (the illustrations provided in FIGS. 1 and 2 are somewhat closer to a real embodiment in that regard) however the illustration is useful in depicting the use of three formed carrier sheets each having a tapered increasing diameter along their length and how they substantially match their diameters when brought together relatively large end to small end. The illustration also depicts that each sensor array element provides 3 capacitive elements and a total of 9 capacitive elements including pairs of electrically conductive regions on the carrier sheets, which occupy almost the full length of the housing. Not shown is the use of filler in the housing to set the position of the sensor array within the housing and to stiffen the housing for making the final product more suitable for use in the field and for transportation.

In another embodiment, a sensor for use in the ground which may include, an elongate hollow elongate housing having a continuously tapered outer wall having a larger maximum outer diameter at a first end compared to the maximum outer diameter of a second end for use in the ground. The sensor has a sensor circuit including at least a portion of a tuned circuit requiring a capacitive element. The sensor circuit is mounted to a circuit board that occupies a portion of the hollow elongate housing.

In this embodiment there is a carrier sheet of flexible material. The carrier sheet has at least two pairs of electrically conductive regions lying between a first edge and a second edge of the carrier sheet. The two electrically conductive regions of a pair of electrically conductive regions are shaped and located near enough each other such that when the carrier sheet is formed into a shape and inserted into the elongate hollow housing the pair of electrically conductive regions they form a capacitive element. Adjacent pairs of capacitive elements have a different diameter and each pair is usable to sense at least the moisture content of the ground surrounding the location of the capacitive element located within the elongate hollow housing.

The invention claimed is:

1. A sensor array for use in a hollow elongate housing having a continuously tapered outer and an inner wall having a larger outer and inner diameter at a first end compared to the outer and inner diameter of a second end for use in the ground, the sensor array includes:
   a carrier sheet of flexible material, the carrier sheet, having one pair of opposite edges of the carrier sheet non-parallel and having at least two pairs of electrically conductive regions lying between a non-parallel first edge and a respective second edge of the carrier sheet, the two electrically conductive regions of a pair of electrically conductive regions are shaped and located near enough each other such that when the carrier sheet is formed into a shape and inserted into the elongate hollow housing the pair of electrically conductive regions form a capacitive element, and adjacent pairs of capacitive elements have a different diameter, each usable to sense at least a moisture content of the ground surrounding the location of the capacitive element located within the elongate hollow housing.

2. A sensor array element according to claim 1 wherein the hollow elongate housing has an inner wall and the sensor array element further includes:
   a centralising arrangement associated with the carrier sheet having at least three contacts with the inner wall of the housing for centralising the carrier sheet within the elongate housing.

3. A sensor array element according to claim 2 wherein the centralising arrangement includes deformable portions of the carrier sheet arranged to project radially outward, when the material is shaped for insertion into the elongate housing, to contact the inner wall of the hollow elongate housing and centralise the formed shape within said hollow elongate housing.

4. A sensor array element according to claim 2 wherein the at least three contacts are substantially evenly radially spaced.

5. A sensor array element according to claim 1 wherein the conductive regions extend from the first edge to the second edge.

6. A sensor array element according to claim 1 wherein the hollow elongate housing has an inner wall, wherein one edge of the carrier sheet includes fixing elements to attach that edge to the carrier sheet when the carrier sheet is formed into a shape to conform to the shape of the inner wall of said hollow elongate housing.

7. A sensor array element according to claim 6 wherein at least one of the fixing elements includes a tang formed by the shape of the flexible material of the carrier sheet being suitable for insertion into a slot in the carrier sheet and for resisting extraction from the slot in the carrier sheet.

8. A sensor array element according to claim 7 wherein the tang has a length and a portion of the tang has a greater width at a free end than the rest of the tang, the carrier sheet having one or more slots located such that when the inserted end of the tang is inserted in the slot the formed carrier sheet has a predetermined diameter at the location of the slot.

9. A sensor array element according to claim 7 wherein the tang arranged to project laterally from an edge of the carrier sheet.

10. A sensor array element according to claim 7, wherein there are multiple slots in the carrier sheet, the slots located such that when a respective tang is inserted into the slot located closer to the edge of the carrier sheet opposite the edge from which a tang projects the predetermined diameter at the location of tang and slot of the formed shape is the largest compared to the use of other slots.

11. A sensor array element according to claim 10, wherein multiple slots are located in the carrier sheet, the slots located such that when a respective tang is inserted into the slot located closer to the edge of the carrier sheet opposite the edge from which a tang projects the predetermined diameter at the location of tang and slot of the formed shape is the smallest compared to the use of other slots.

12. A sensor array element according to claim 1 wherein there are three pairs of conductive regions on a carrier sheet.

13. A sensor array element according to claim 1 wherein the carrier sheet has three pairs of conductive regions wherein each pair of conductive regions forms a different maximum outer diameter capacitive element each being at least one capacitive element of a respective tuned circuit.

14. A sensor array element according to claim 1 wherein end of each conductive region is adapted to be electrically conductively connected to a circuit board.

15. A sensor array element according to claim 1 wherein the same size carrier sheet can be used anywhere within the housing, the carrier sheet having multiple slots and multiple tangs, the tangs usable for engagement with respective slots to provide successively smaller diameter shaped carrier sheets along the length of the carrier sheet when shaped suitable for insertion into the elongate hollow housing, such that multiple carrier sheets are locatable along the length of the elongate hollow housing from the first end to the second end of the elongate hollow housing.

16. A sensor for use in the ground, including:
an elongate hollow housing having a continuously tapered outer wall and an inner wall having a larger outer and inner diameter at a first end compared to the outer and inner diameter of a second end for use in the ground;
a sensor circuit including at least a portion of a tuned circuit requiring a capacitive element, the circuit mounted to a circuit board that occupies a portion of the hollow elongate housing; and
a carrier sheet of flexible material, the carrier sheet, having one pair of opposite edges of the carrier sheet non-parallel and having at least two pairs of electrically conductive regions lying between a non-parallel first edge and a respective second edge of the carrier sheet, the two electrically conductive regions of a pair of electrically conductive regions are shaped and located near enough each other such that when the carrier sheet is formed into a shape and inserted into the elongate hollow housing the pair of electrically conductive regions form a capacitive element when connected to the sensor circuit, and adjacent pairs of capacitive elements have a different diameter, each usable to sense at least a moisture content of the ground surrounding the location of the capacitive element located within the elongate hollow housing.

17. A sensor array for use in an elongate hollow housing having a larger outer and inner diameter at a first end than the second end for use in the ground, the sensor array including:
a sensor circuit including at least a portion of a tuned circuit requiring a capacitive element, the circuit mounted to a circuit board having at least two circuits and the circuit board adapted in size to occupy a portion of the hollow elongate housing; and
a carrier sheet of flexible material, the carrier sheet, having one pair of opposite edges of the carrier sheet non-parallel and having at least two pairs of electrically conductive regions lying between a non-parallel first edge and a respective second edge of the carrier sheet, the two electrically conductive regions of a pair of electrically conductive regions are shaped and located near enough each other such that when the carrier sheet is formed into a shape and inserted into the elongate hollow housing the pair of electrically conductive regions form a capacitive element when connected to the sensor circuit, and adjacent pairs of capacitive elements have a different diameter, each usable to sense at least a moisture content of the ground surrounding the location of the capacitive element located within the elongate hollow housing.

* * * * *